(12) United States Patent
Shores et al.

(10) Patent No.: US 8,518,065 B2
(45) Date of Patent: *Aug. 27, 2013

(54) SURGICAL INSTRUMENT WITH TELESCOPING ATTACHMENT

(75) Inventors: Rex Wesley Shores, The Colony, TX (US); James Q. Spitler, Midlothian, TX (US); Dana A. Eskridge, Ojai, CA (US); Dennis L. Foster, Ojai, CA (US); Douglas W. Haight, Camarillo, TX (US); Laura A. Kriese, Ventura, CA (US); Stephen G. Savage, Oxnard, CA (US); Danny C. Riedel, Weatherford, TX (US)

(73) Assignee: Medtronic, Inc., Minneapolis, MN (US)

( * ) Notice: Subject to any disclaimer, the term of this patent is extended or adjusted under 35 U.S.C. 154(b) by 1307 days.

This patent is subject to a terminal disclaimer.

(21) Appl. No.: 12/114,506

(22) Filed: May 2, 2008

(65) Prior Publication Data

US 2008/0208195 A1     Aug. 28, 2008

Related U.S. Application Data

(63) Continuation of application No. 10/326,178, filed on Dec. 20, 2002, now Pat. No. 7,559,927.

(51) Int. Cl.
*A61B 17/32* (2006.01)

(52) U.S. Cl.
USPC .............................. 606/167; 606/79; 606/205

(58) Field of Classification Search
USPC ............. 606/80, 180, 170, 167, 79, 159, 168, 606/169, 205–209, 1; 279/75, 143; 433/129; 600/568

See application file for complete search history.

(56) References Cited

U.S. PATENT DOCUMENTS

| | | |
|---|---|---|
| 2,807,473 A | 9/1957 | Kiehne |
| 3,384,085 A | 5/1968 | Hall et al. |
| 3,835,858 A | 9/1974 | Hagen |
| 4,203,222 A | 5/1980 | Matchen |
| 4,265,231 A | 5/1981 | Scheller, Jr. et al. |
| 4,298,074 A | 11/1981 | Mattchen |
| 4,699,550 A | 10/1987 | Baker |
| 4,728,876 A | 3/1988 | Mongeon et al. |
| 5,152,744 A | 10/1992 | Krause et al. |

(Continued)

FOREIGN PATENT DOCUMENTS

| | | |
|---|---|---|
| DE | 10107156 A1 | 9/2002 |
| WO | 02/076308 | 10/2002 |

OTHER PUBLICATIONS

Office Action mailed Nov. 14, 2008 in U.S. Appl. No. 10/698,177, filed Oct. 31, 2003.

(Continued)

*Primary Examiner* — S. Thomas Hughes
*Assistant Examiner* — Tin Nguyen
(74) *Attorney, Agent, or Firm* — Harness, Dickey

(57) ABSTRACT

A surgical instrument for the dissection of bone and other tissue includes a spindle, a dissection tool and a coupler disposed between the spindle and the dissection tool. The coupler includes a tool collet and an attachment locking mechanism operable to permit tool collet operation and telescoping movement of an attachment tube with respect to the dissection tool. A method is also provided for convenient coupling of the dissection tool and adjustment of the attachment tube length.

23 Claims, 13 Drawing Sheets

(56) References Cited

U.S. PATENT DOCUMENTS

| | | | |
|---|---|---|---|
| 5,222,956 A | 6/1993 | Waldron | |
| 5,320,635 A | 6/1994 | Smith | |
| 5,330,480 A | 7/1994 | Meloul et al. | |
| 5,340,129 A | 8/1994 | Wright | |
| 5,347,988 A | 9/1994 | Hori | |
| 5,380,333 A | 1/1995 | Meloul et al. | |
| 5,439,005 A * | 8/1995 | Vaughn | 600/568 |
| 5,490,683 A | 2/1996 | Mickel et al. | |
| 5,505,737 A | 4/1996 | Gosselin et al. | |
| 5,529,580 A | 6/1996 | Kusunoki et al. | |
| 5,569,256 A * | 10/1996 | Vaughn et al. | 606/80 |
| 5,593,416 A | 1/1997 | Donahue | |
| 5,601,560 A | 2/1997 | Del Rio et al. | |
| 5,630,818 A | 5/1997 | Del Rio et al. | |
| 5,741,263 A | 4/1998 | Umber et al. | |
| 5,779,404 A | 7/1998 | Jore | |
| 5,782,836 A | 7/1998 | Umber et al. | |
| 5,833,704 A | 11/1998 | McCombs et al. | |
| 5,851,208 A * | 12/1998 | Trott | 606/80 |
| 5,888,200 A | 3/1999 | Walen | |
| 5,893,851 A | 4/1999 | Umber et al. | |
| 5,904,687 A | 5/1999 | Del Rio et al. | |
| 5,913,859 A | 6/1999 | Shapira | |
| 5,928,238 A | 7/1999 | Scarborough et al. | |
| 5,928,241 A | 7/1999 | Menut et al. | |
| 5,941,891 A | 8/1999 | Walen | |
| 5,989,257 A | 11/1999 | Tidwell et al. | |
| 5,993,453 A | 11/1999 | Bullara et al. | |
| 5,993,454 A | 11/1999 | Longo | |
| 6,033,408 A | 3/2000 | Gage et al. | |
| 6,062,575 A | 5/2000 | Mickel et al. | |
| 6,209,886 B1 * | 4/2001 | Estes et al. | 279/50 |
| 6,270,087 B1 | 8/2001 | Mickel et al. | |
| RE37,358 E | 9/2001 | Del Rio et al. | |
| 6,312,438 B1 | 11/2001 | Adams | |
| 6,423,070 B1 | 7/2002 | Zeppelin | |
| 6,457,916 B2 | 10/2002 | Weinhold | |
| 6,562,055 B2 | 5/2003 | Walen | |
| 6,616,149 B1 | 9/2003 | Pjevach et al. | |
| 6,733,218 B2 | 5/2004 | Del Rio et al. | |
| 6,766,218 B2 | 7/2004 | Rosenblum | |
| 7,001,391 B2 | 2/2006 | Estes | |
| 7,549,992 B2 | 6/2009 | Shores et al. | |
| 2001/0043841 A1 | 11/2001 | Wienhold | |
| 2003/0023256 A1 | 1/2003 | Estes et al. | |
| 2004/0122460 A1 | 6/2004 | Shores et al. | |
| 2006/0178672 A1 | 8/2006 | Shores et al. | |

OTHER PUBLICATIONS

Medtronic Brochure, "Midas Rex Classic Dissecting Tool Guide", Printed in USA, 2000.

Medtronic Brochure, "Midas Rex Classis System", Printed in USA, 2000.

* cited by examiner

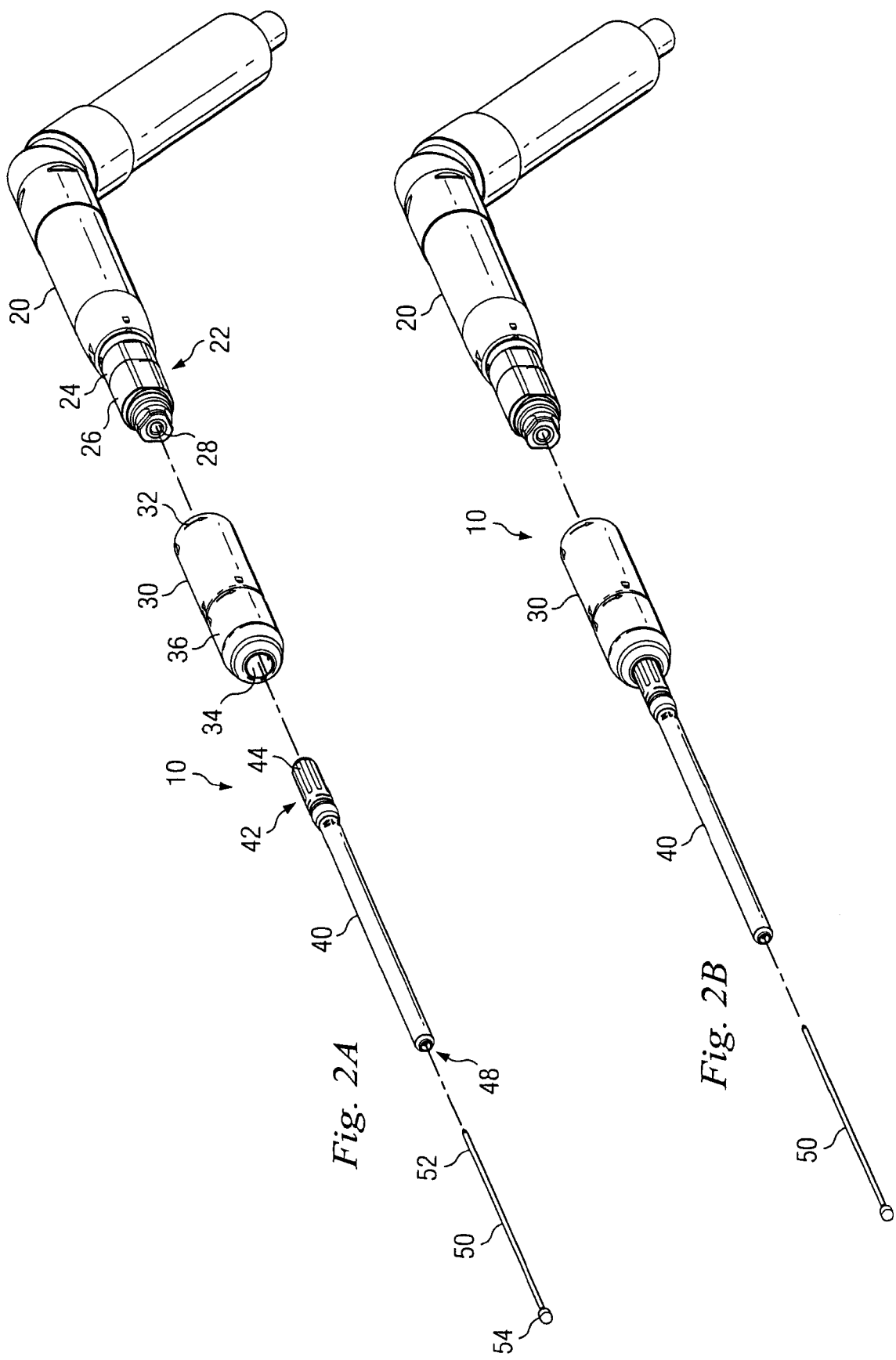

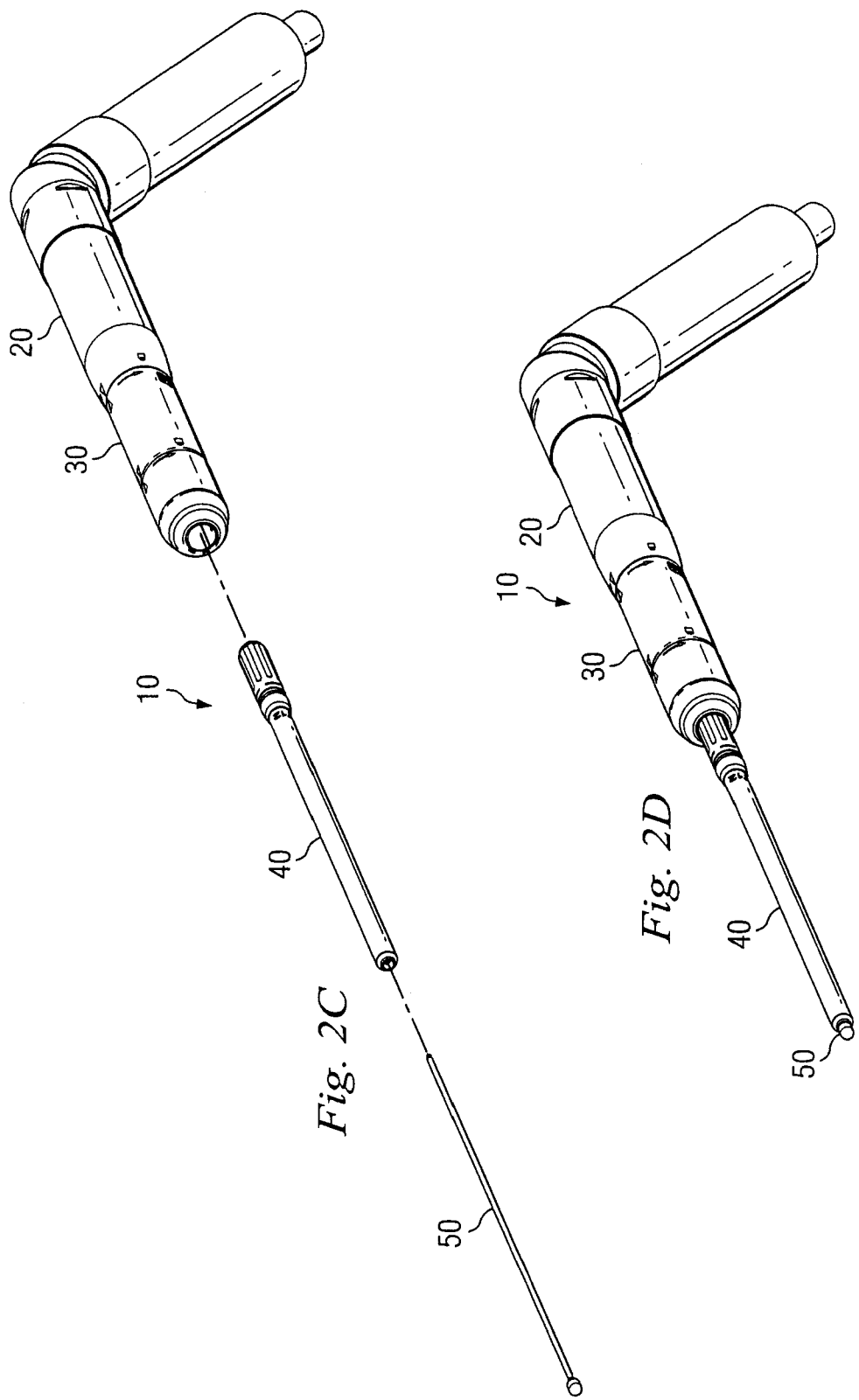

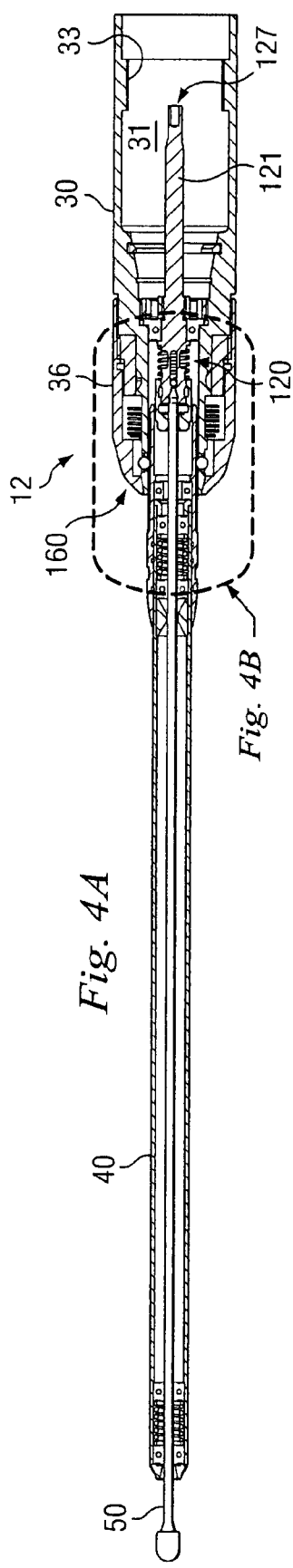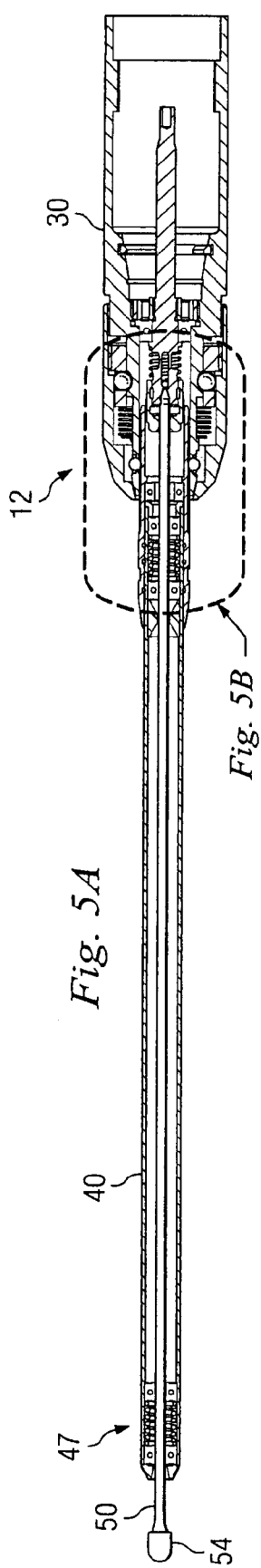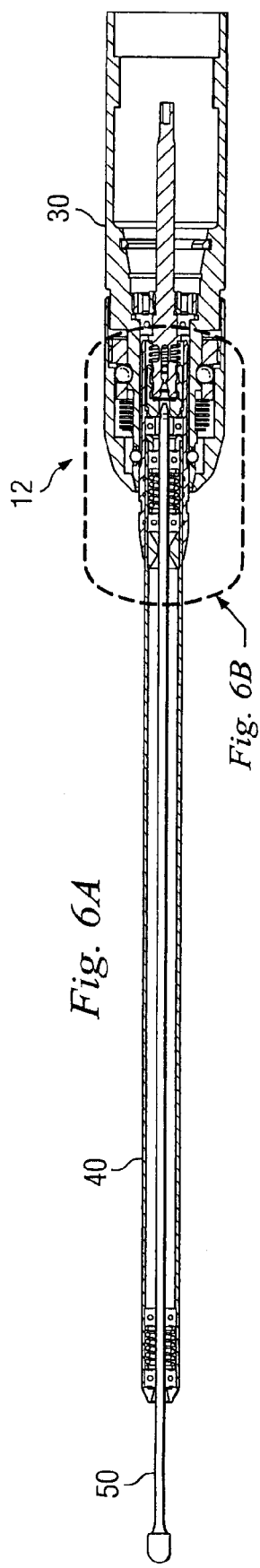

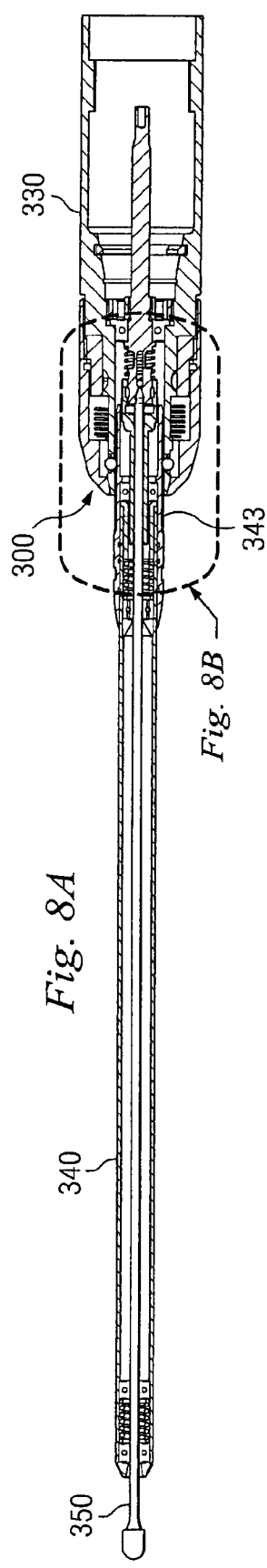
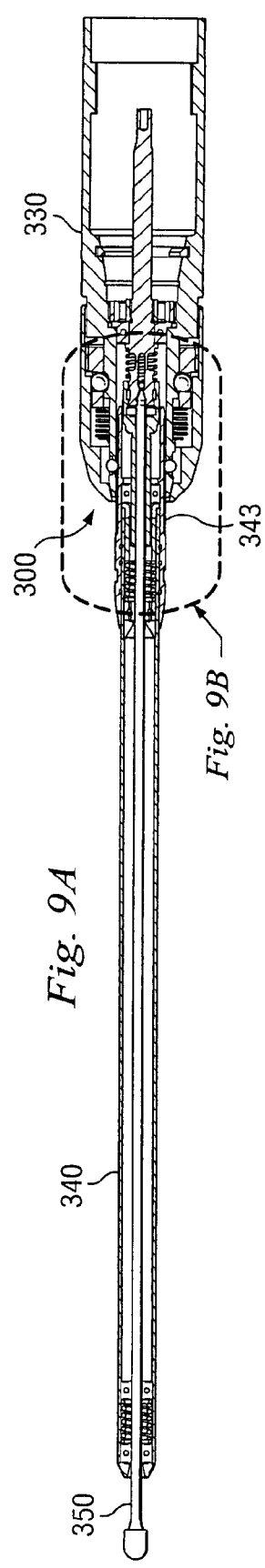
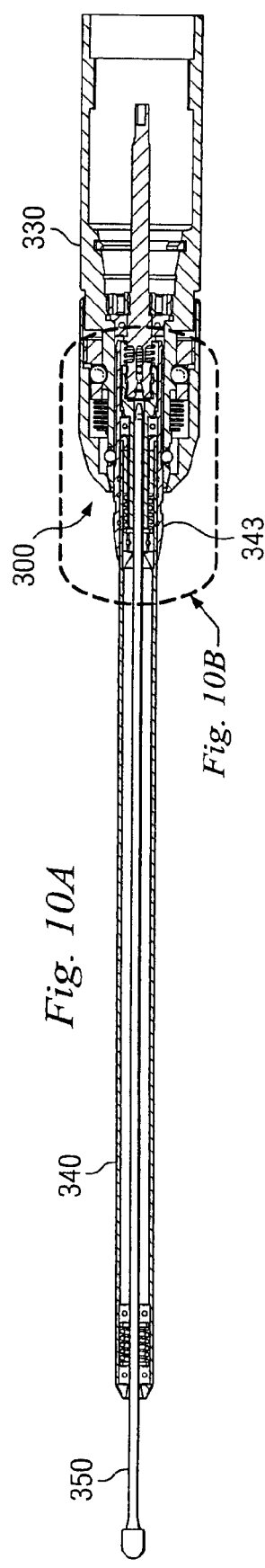

SURGICAL INSTRUMENT WITH TELESCOPING ATTACHMENT

CROSS-REFERENCE TO RELATED APPLICATION

The present disclosure is a continuation of and claims priority to U.S. Ser. No. 10/326,178, filed Dec. 20, 2002, and entitled, "Surgical Instrument with Telescoping Attachment," hereby incorporated by reference in its entirety.

FIELD OF THE INVENTION

The present invention generally relates to surgical instruments for use in the dissection of bone and other tissue. More particularly, the present invention relates to a telescoping attachment for a surgical instrument.

BACKGROUND OF THE INVENTION

In various surgical procedures, it is necessary to dissect bone or other tissue. Many conventional surgical instruments used for the dissection of bone or other tissue employ pneumatic or electrical motors to rotate a cutting element. In their most basic form, such surgical instruments comprise a motor portion having a rotary shaft, a dissection tool having a cutting or abrading element that is moved by the rotating shaft of the motor, and a coupling arrangement for connecting the dissection tool to a spindle or collet of the rotary shaft. The spindle or collet of the rotary shaft is usually housed within a base that is attached to the motor.

Because it is frequently necessary to replace the dissection tool, it is also known in the art to use a quick release coupling to secure the dissection tool to the surgical instrument. An example of such a quick release coupling is shown and described in commonly assigned U.S. Pat. No. 5,505,737 entitled "Quick Release Coupling For A Dissecting Tool" incorporated herein by reference. The coupling device shown in U.S. Pat. No. 5,505,737 includes a spindle attachment which is secured to a spindle of a surgical instrument. The spindle attachment has a shaft engagement portion for engaging a shaft of the dissection tool. The shaft engagement portion of the spindle attachment is provided with apertures that terminate within a central bore of the engagement portion through which the shaft of the dissection tool extends.

Powered surgical dissection instruments often utilize dissection tools having small shaft diameters in relation to their length. Such shafts may bend or flail in use if not adequately supported. This occurrence may be heightened when such shafts are used with motors that are designed to reach speeds in excess of 72,000 rpm. Tool makers have provided attachments or tubes that engages the motor portion and receive a portion of the dissection tool shaft. Typically, such an attachment will include one or more bearing that support the dissection tool shaft at it extends from the tool collet. Attachments may be provided with many configurations varying by length, diameter and function. While telescoping attachments have been utilized which provide the capability of varying the distance the distal tip of the tube extends from the motor housing, the installation and adjustment of such devices remains cumbersome.

While known surgical tools include adjustable components, a need exists in the pertinent art for an improved surgical tool which permits telescoping of the attachment relative to the motor.

SUMMARY OF THE INVENTION

In one particular embodiment, the surgical instrument includes a coupler for telescopingly engaging an attachment tube to a surgical motor. In a preferred, but not required, aspect of the illustrated embodiment, the coupling assembly may be manually manipulated to permit tool collet locking and attachment tube adjustment without removal from the motor.

Additional advantages and features of the present invention will become apparent from the following description and appended claims, taken in conjunction with the accompanying drawings.

Further areas of applicability of the present invention will become apparent from the detailed description provided hereinafter. It should be understood that the detailed description and specific examples, while indicating the preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 2A is a partially exploded perspective view of an embodiment of a surgical dissection tool according to the present invention.

FIG. 2B is a partially exploded perspective view of the embodiment of FIG. 2A.

FIG. 2C is a partially exploded perspective view of the embodiment of FIG. 2A.

FIG. 2D is an assembled perspective view of the embodiment of FIG. 2A.

FIGS. 4A and 4B are partial cross-sectional side views of the embodiment of FIG. 3 in an assembled and locked position.

FIGS. 5A and 5B are partial cross-sectional side views of the embodiment of FIG. 3 in an assembled and partially unlocked position.

FIGS. 6A and 6B are partial cross-sectional side views of the embodiment of FIG. 3 in an assembled and unlocked position.

FIGS. 8A and 8B are partial cross-sectional side views of the embodiment of FIG. 7 in an assembled and locked position.

FIGS. 9A and 9B are partial cross-sectional side views of the embodiment of FIG. 7 in an assembled and partially unlocked locked position.

FIGS. 10A and 10B are partial cross-sectional side views of the embodiment of FIG. 7 in an assembled and unlocked position.

DETAILED DESCRIPTION OF THE PREFERRED EMBODIMENTS

The following description of the preferred embodiments is merely exemplary in nature and is in no way intended to limit the invention, its application, or uses.

Figure 1:
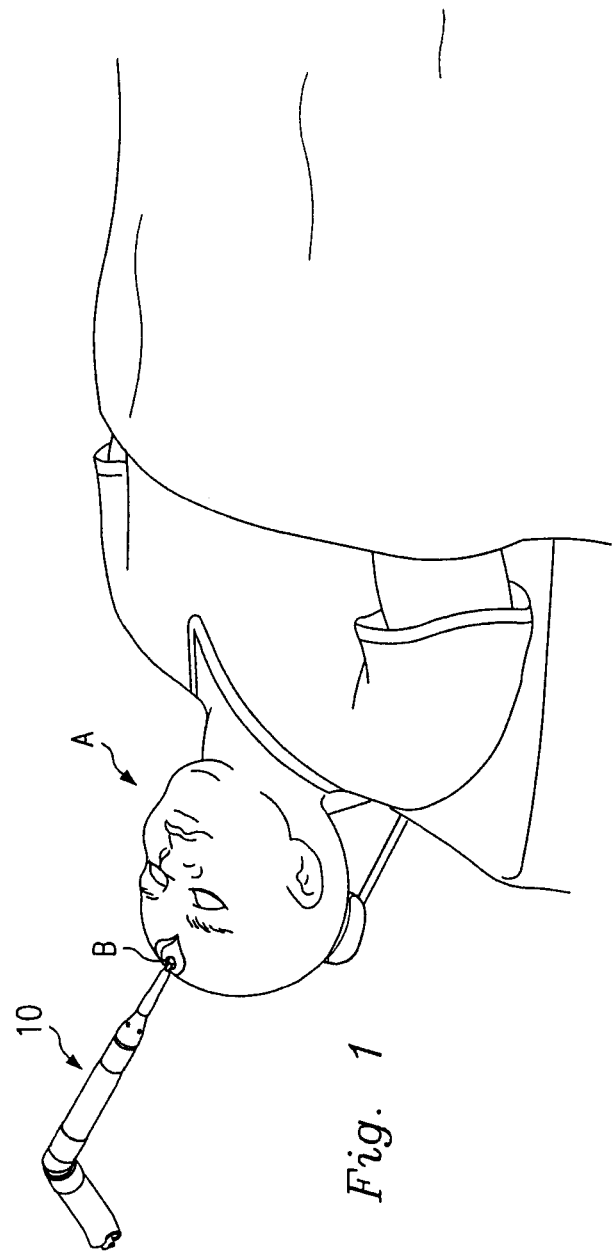
FIG. 1 is an illustration of a surgical dissection tool according to the present invention used in a human patient.

Referring now to FIG. 1, there is shown a human patient A undergoing a neurological operation. As is common practice, access to the brain or other neurological structures often requires delicate dissection of bone and other tissues B to gain access. By way of example, dissection tool assembly 10 in accordance with one aspect of the present invention is shown being utilized to dissect a portion of patient A's bone and other tissue B adjacent to the surgical access site.

Referring now to FIGS. 2A through 2D, a dissection tool assembly 10 for the dissection of bone or other tissue is illustrated. A pneumatic motor 20 is illustrated having a collet assembly 22 disposed on its distal end. Collet assembly 22 will not be described in great detail in the present application as it is more fully disclosed in a prior filed application U.S. Ser. No. 10/200,683 filed Jul. 22, 2002, entitled "Surgical Instrument with Rotary Cutting Member and Quick Release Coupling Arrangement" incorporated by reference herein in its entirety. Collet assembly 22 includes a proximal movable portion 24 and a distal fixed portion 26. A shaft receiving aperture 28 is provided on the distal end to slidably receive a rotary shaft. The dissection tool assembly 10 further includes an attachment base coupling assembly 30 adapted to be received about collet assembly 22 and having an attachment aperture 34 at its distal length. An attachment tube 40 is provided having a proximal portion 42 with grooves 44 extending along a portion thereof. The distal end of attachment tube 40 includes a tool receiving aperture 48. The coupling assembly 30 and attachment tube 40 may be combined to form a telescoping attachment assembly 12. An exemplary illustration of a dissection tool 50 is also shown. Dissection tool 50 includes an elongated shaft 52 and a tissue dissection head 54.

Figure 3:
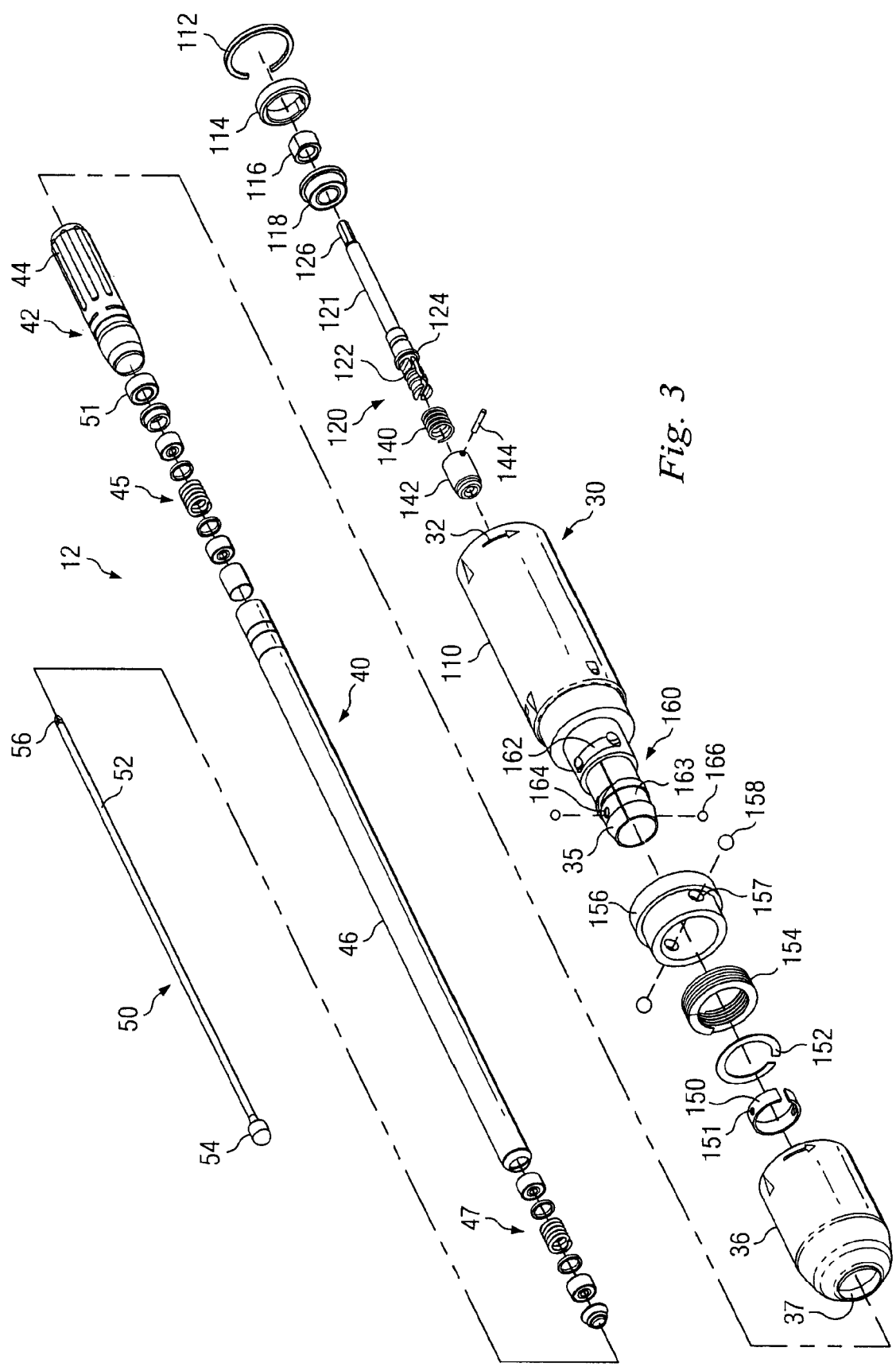
FIG. 3 is an exploded perspective view of an embodiment of a telescoping attachment assembly according to the present invention.

Referring now to FIG. 3, there is shown an exploded perspective view of the components of telescoping attachment assembly 12 according to one embodiment of the present invention. Telescoping attachment assembly 12 includes coupling assembly 30 and attachment 40. Dissection tool 50 is illustrated for purposes of completeness; however, it is not a required component of telescoping attachment assembly 12 but is shown for use in cooperation with the telescoping attachment assembly. Attachment assembly 30 includes a body 110 having an outer surface and defining an axially disposed internal passage 31 (FIG. 4A) extending substantially the length of body 110. Tool coupling assembly 120 is disposed within internal passage 31. Tool coupling assembly 120 includes a split ring 112, a bearing 114, a retaining ring 116, a bearing 118 disposed about the proximal portion of a rotor shaft 121. Rotor shaft 121 includes a circumferential shoulder 124 and a proximal gripping end 122. A spring 140 is disposed adjacent shoulder 124 and a locking sleeve 142 is circumferentially disposed about gripping end 122 and held in position by pen 144.

The distal end of coupling assembly 30 comprises attachment locking assembly 160. Attachment locking assembly includes distal portion 36, tension ring 150 having apertures 151 disposed therein, split ring 152, spring 154, collar 156 having apertures 157 and locking ball 158 disposed therein. Balls 166 are disposed within apertures 151 in their assembled condition and similarly extend through apertures 164 disposed in body 110. Body 110 further defines collet fingers 163 at its distal extreme. A helical groove 162 is provided to receive locking balls 158. Helical groove 162 further includes shallow detents at either end of its length. It will be understood that these shallow detents provide a provisional locking of the locking balls when they reach this position, thereby maintaining the assembly in the select position. This may also provide the user with tactile feedback as the balls fall into the detents.

Attachment tube 40 comprises proximal portion 42 having a plurality of axially aligned grooves 44 disposed on the exterior surface. A proximal bearing assembly 45 is shown having a number of bearings, rings and a tension spring illustrated there between. Bearing 51 is disposed proximally of proximal bearing assembly 45. Attachment tube 40 also includes a distal bearing assembly 47. Proximal bearing assembly 45 and distal bearing assembly 47 are fixably disposed within tube 46 and are preferably adapted to support a rotating shaft. Proximal portion 42 is fixably attached to the exterior of tube 46 and retains bearing 51 in position.

Figure 4B:
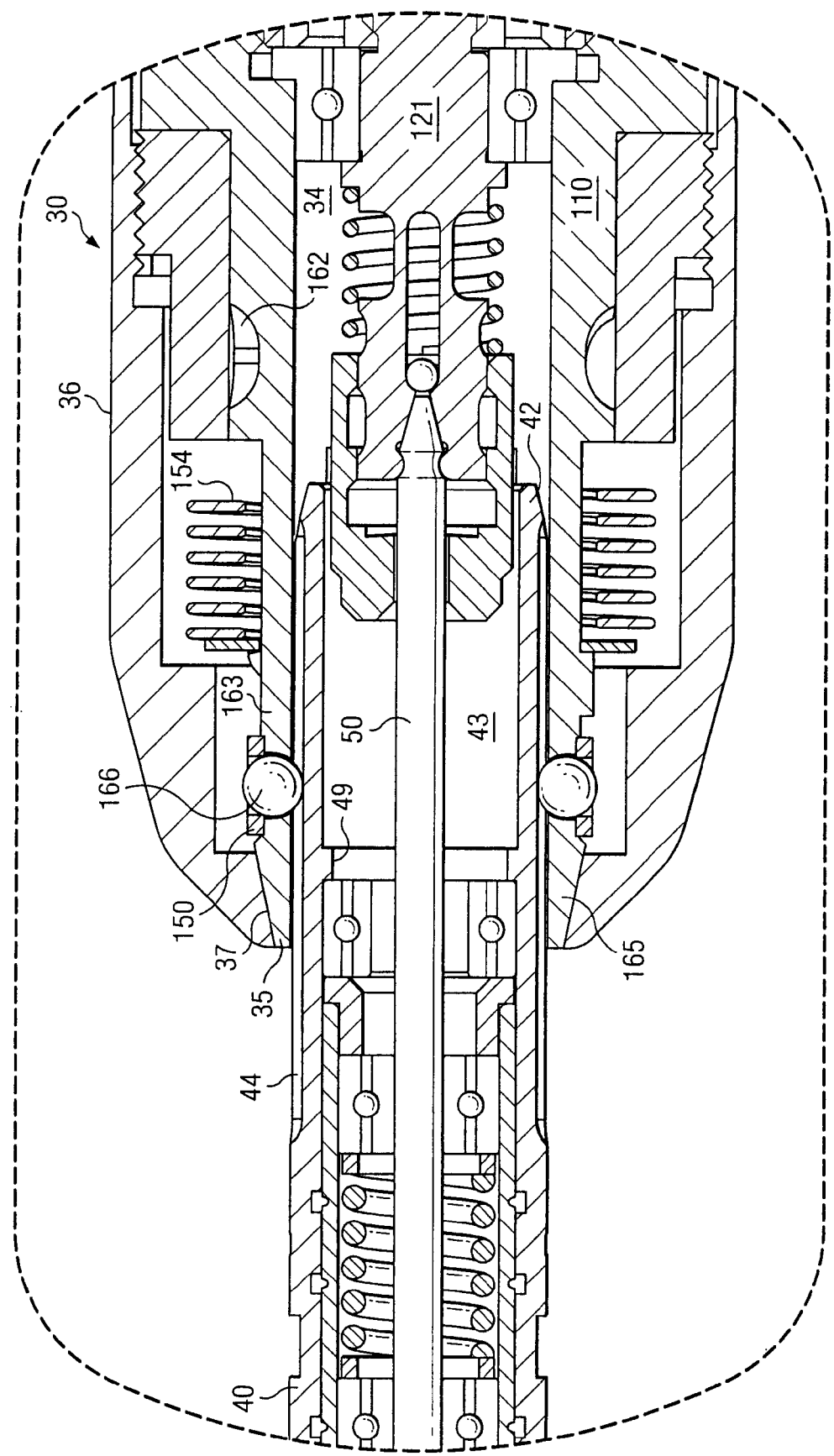

Referring now to FIGS. 4A through 6B, the details of tool coupling assembly 120 and attachment of locking assembly 160 will be more fully described. Cross-sectional view of FIGS. 4A and 4B show telescoping attachment assembly 12 in the fully locked position. Dissection tool 50 is locked within tool coupling assembly 120 and attachment tube 40 is locked within attachment locking assembly 160. As shown more fully in FIG. 4B, proximal portion 42 of attachment tube 40 extends within internal chamber 34 of coupling assembly 30. Ball 166 is disposed within groove 44 and is retained in this position by tension ring 150. Distal portion 36 has been rotated to the locked position moving balls 158 within helical groove 162 to axially displace distal portion 36 in the proximal direction. As distal portion 36 moves in the proximal direction, an internal tapered surface 37 engages an external tapered surface 35 of collet fingers 163. The engagement between internal tapered surface 37 and external tapered surface 35 and the corresponding surface on collet finger 165 urges the attachment locking assembly 160 to constrict the diameter of attachment aperture 34 and thereby lockingly engage proximal portion 42 of attachment tube 40. In this position, axially displacement of attachment tube 40 with respect to coupling assembly 30 is inhibited.

Figure 5B:
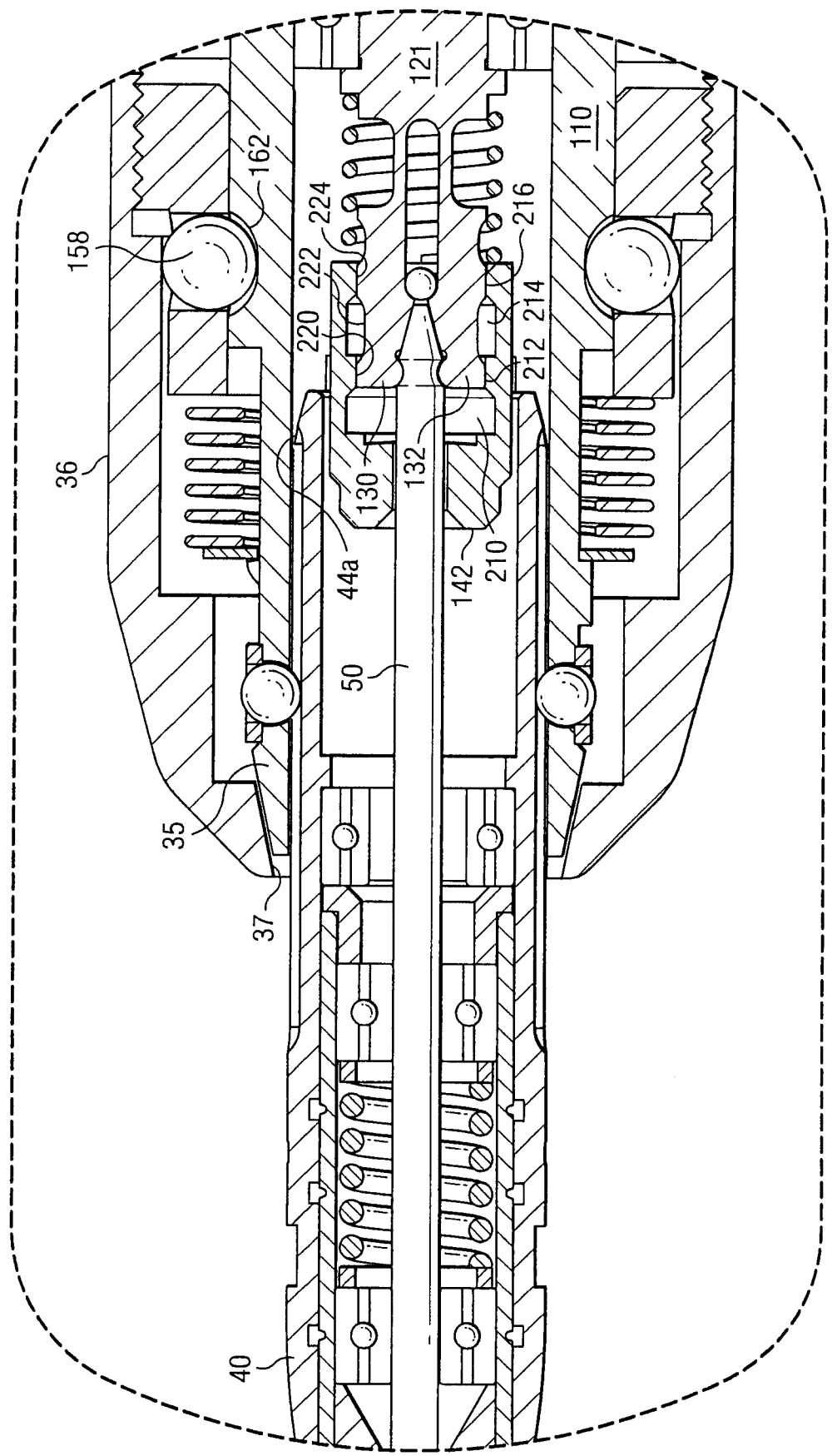

Referring now specifically to FIGS. 5A and 5B, telescoping attachment assembly 12 is shown with the attachment locking assembly 160 in an unlocked position and with tool coupling assembly 120 in a locked position. Distal portion 36 has been rotated with respect to motor 20 to urge balls 158 within helical groove 162. Movement of the balls 158 within helical groove 162 urges distal portion 36 to be axially displaced in a distal direction with respect to motor 20. Such distal displacement along the axis causes internal tapered surface 37 to be disengaged from external tapered surface 35 such that attachment aperture 34 effectively expands in diameter. In this state, attachment tube 40 may be slidably displaced within attachment aperture 34. Groove 44 is formed on proximal portion 42 such that it does not extend to the extreme proximal end and thereby creates a proximal shoulder 44*a*. The engagement of ball 166 in groove 44 may thereby provide a tactile feedback to the user when ball 166 is initially engaged in groove 44. With distal movement of the attachment tube 40 engaged in the locking assembly 160, resistance upon engagement of ball 166 against shoulder 44*a* provides tactile feedback to the user that attachment tube 40 is about to be disengaged from coupling assembly 30. Further distal movement of attachment tube 40 causes ball 166 to overcome the compressive force of tension ring 150 such that the attachment may be completely removed from aperture 34.

Figure 6B:
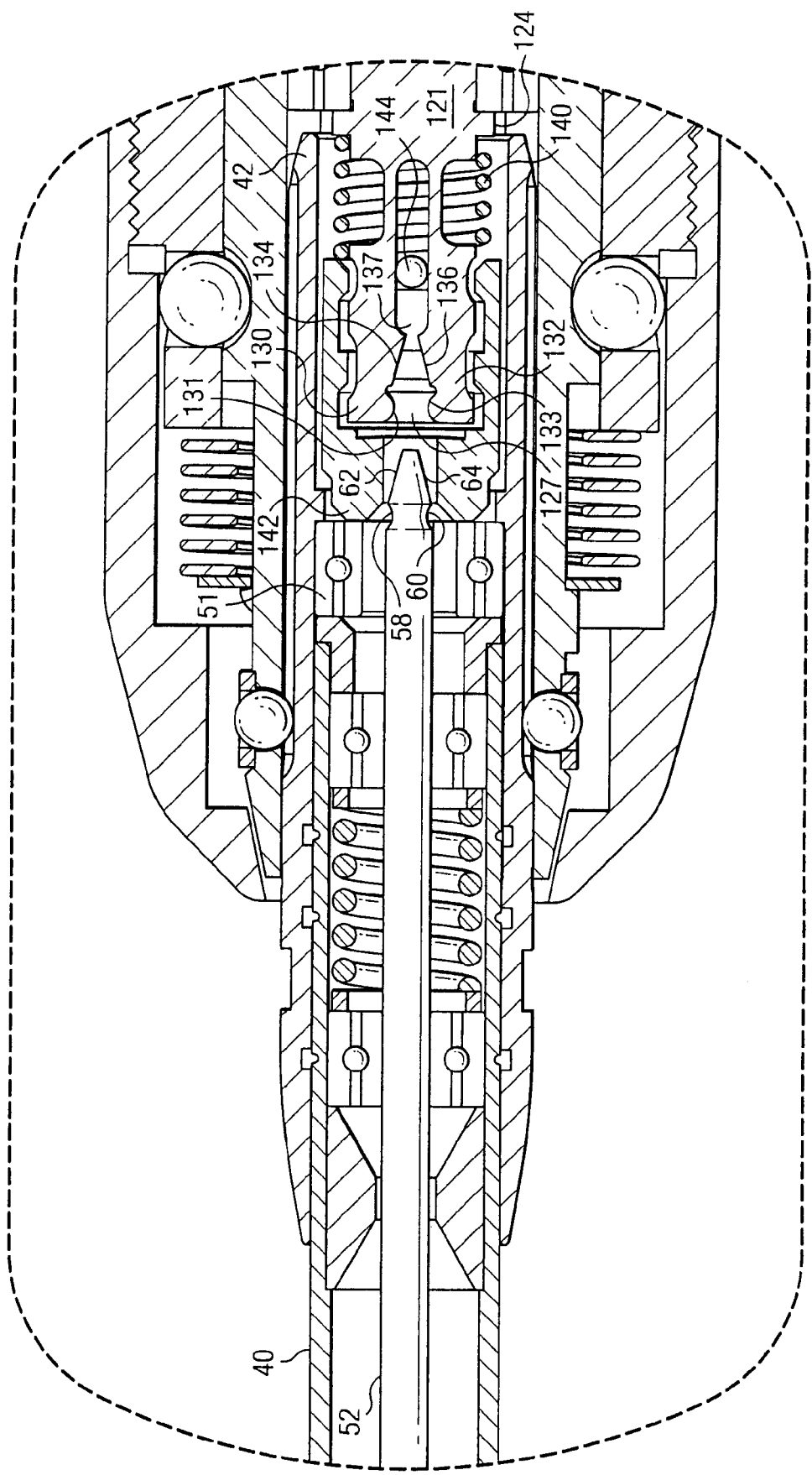

Referring now to FIGS. 3, 5B and 6B, there are shown details of the tool coupling assembly 120. Tool coupling assembly includes a locking sleeve 142 disposed about gripping end 122. Locking sleeve 142 includes an internal bore with a relief area 210, a projection 212, a further relief area 214 and a further projection 216. Gripping end 122 includes first gripping finger 130 and a second complementary gripping finger 132. The gripping fingers include a first ridge 220, a relief 222 and a second ridge 224, defined on their outer surface as shown in FIG. 5B. The internal surface of gripping finger 130 includes a projection 131 and a driving surface 134. In a similar manner, gripping finger 132 includes a projection 133 and a driving surface 136. It will be understood that these driving surfaces and projections are substantially complementary to corresponding features of recesses 58 and 60 and driving surfaces 62 and 64 of dissection tool 50. As shown in FIG. 4B, the internal surfaces of the tool coupling assembly 120 substantially correspond to and mate with the external features of the dual driving pattern 56 to thereby retain the tool and effectively provide rotary force thereto. Locking sleeve 142 is retained on gripping end 122 by means of pin 144 passing through a portion of the locking sleeve and extending through a slot 137 defined between gripping finger 130 and gripping finger 132.

Tool coupling assembly 120 has a normally locked position such as that shown in FIG. 4B and a second unlocked position shown in FIG. 6B. In the locked position at FIG. 4B, projection 212 is in substantial axially alignment with ridge 220 and projection 216 is in substantial axially alignment with ridge 224 thereby urging gripping fingers 130 and 132 into the locked position. In the second unlocked position illustrated in FIG. 6B, projection 212 is in substantial axially alignment with relief 222 and projection 216 is disposed proximally of ridge 216. In a similar fashion, relief area 210 is disposed adjacent ridge 220 and relief area 214 is disposed adjacent ridge 224. In this position, gripping fingers 130 and 132 may move to their release position such that dissection tool 50 may be removed from tool coupling assembly 120. It will be appreciated that spring 140 acts on locking sleeve 142 to urge the locking sleeve into the first locked position. As shown in FIG. 6B, attachment proximal portion 42 is moved to the extreme proximal portion of attachment aperture 34 bringing bearing 51 into contact with locking sleeve 142 whereby further proximal movement of attachment tube 40 causes the locking sleeve to move into the second unlocked position shown in FIG. 6B. Bearing 51 is provided as the contact surface between attachment tube 40 and locking sleeve 142 in the event that power would be applied to rotor shaft 121. It will be understood that bearing 151 may rotate with locking sleeve 142 to thereby isolate rotary force from being transmitted to attachment tube 40. As attachment tube 40 is moved distally, spring 144 urges locking sleeve 142 into the first locked position shown in FIG. 4B.

Dissection assembly tool 10 may be assembled in the following manner, although the present invention is not limited to a specific sequence of assembly. As shown at FIGS. 2A-2D, coupling assembly 30 may be slidably advanced over collet assembly 22 of motor 20. As described in the prior filed application entitled "Surgical Instrument with Rotary Cutting Member and Quick Release Coupling Arrangement", U.S. Ser. No. 10/200,683 filed Jul. 22, 2002, axial rotation of coupling assembly 30 about motor 20 causes rotational movement of movable portion 24 thereby actuating an internal collet locking mechanism of motor 20 to rotationally mate with drive pattern 126 of rotor shaft 121 (see FIG. 3). In a preferred aspect, rotation of coupling assembly 30 about motor 20 also locks the coupling assembly to the motor. In the illustrated embodiment, the amount of rotation necessary to move from an unlocked position to a locked position is approximately 90 degrees. As best seen in FIG. 4A, coupling assembly 30 includes a pair of internal flats 33 disposed within internal chamber 31. It will be appreciated that as the coupling assembly 30 is slidably advanced with respect to motor 20, flats 33 will engage corresponding flats on collet assembly 22 to properly orient the two components. Moreover, upon rotation of coupling assembly 30 about motor 20, flats 33 will drive movable portion 24 to operate the internal tool locking mechanism as well as being positioned behind fixed portion 26 such that the coupling assembly is fixably engaged with motor 20.

Attachment tube 40 may be axially advanced within attachment aperture 34. Grooves 44 may be positioned within attachment aperture 34 such that retaining balls 166 (FIG. 4B) provisionally retain the attachment tube 40 within coupling assembly 30. In the provisional retention state (FIG. 5B), attachment tube 40 may be axially displaced within coupler 30. With the attachment joined to the coupler, dissection tool 50 may then be inserted through tool aperture 48 until the driving pattern 56 is disposed adjacent the tool coupling assembly 120 of the coupling assembly 30. Attachment tube 40 may be then be moved along its longitudinal axis distally toward motor 20 to thereby open the tool coupling assembly 120 and the driving pattern 56 may then be advanced into a locking position. Distal movement of attachment tube 40 away from motor 20 results in dissection tool 50 being coupled to coupling assembly 30. Attachment tube 40 may then be moved with respect to coupling assembly 30 to vary the distance between distal bearing 47 and dissection head 54. Once the desired displacement has been obtained, distal portion 36 may be rotated approximately 90 degrees in the direction of arrow 38 with respect to motor 20 to thereby lock the position of attachment tube 40 with respect to coupling assembly 30.

Disassembly of the dissection tool assembly 10 may be performed in substantially the inverse order of operations described above to assemble the tool. More specifically, distal portion 36 may be rotated in an opposite direction with respect to motor 20 thereby permit axial movement of attachment tube 40 with respect to coupling assembly 30. Attachment tube 40 may then be moved proximally to engage the tool coupling assembly 120 and move it to an unlocked position. Dissection tool 50 may then be withdrawn from the tool coupling assembly 120 and from attachment tube 40. Thereafter, attachment tube 40 may be removed from coupling assembly 30 or a new dissection tool may be inserted through the attachment into locking engagement with coupling assembly 30. It will be appreciated that coupling assembly 30 may be quickly and easily removed from motor 20 by rotation in the opposite direction of arrow 32 to move movable portion 24 to its unlocked position. This may be accomplished with dissection tool 50 and attachment tube 40 fully engaged in the distal end of coupling assembly 30.

Figure 7:
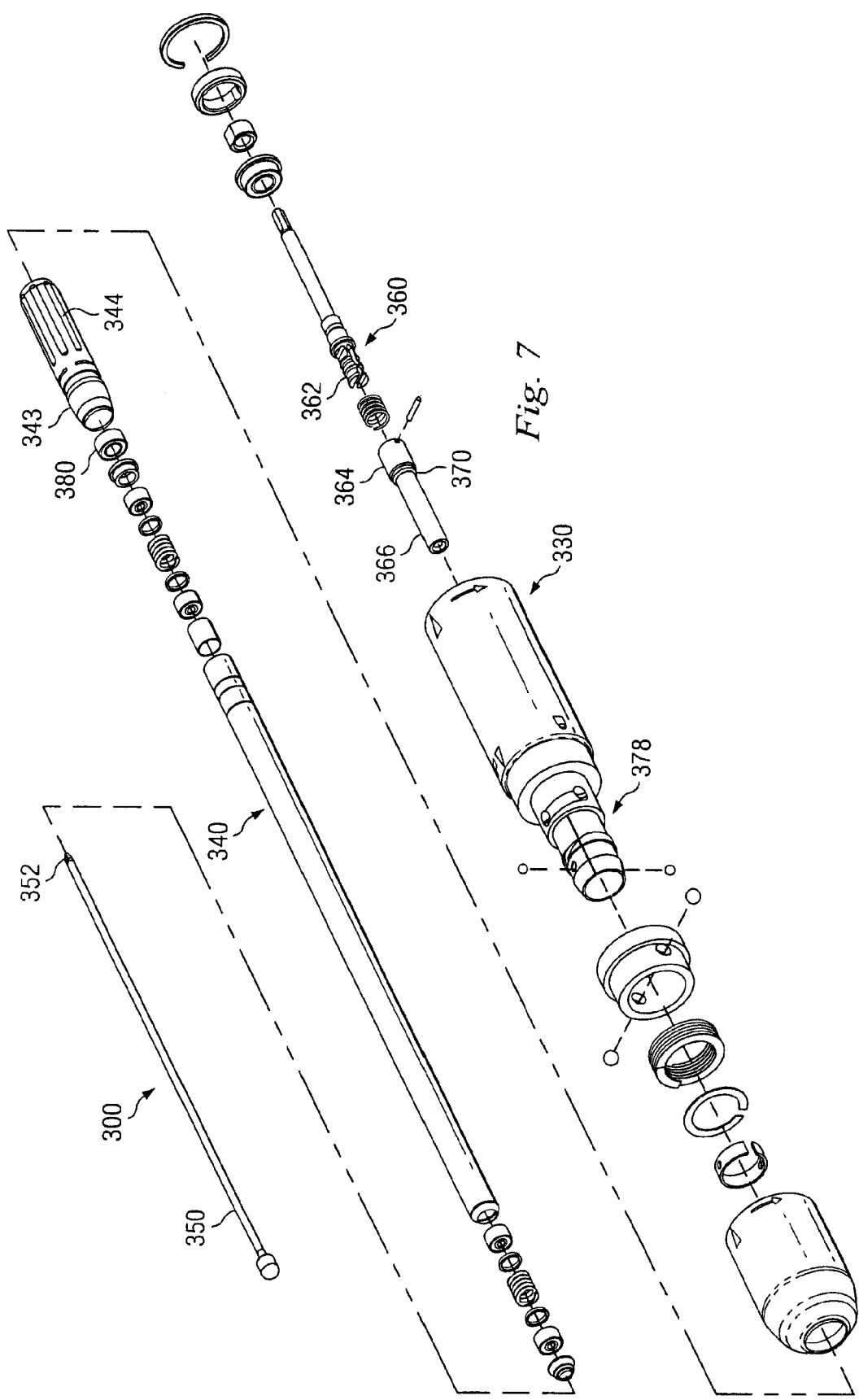
FIG. 7 is an exploded perspective view of an embodiment of a telescoping attachment assembly according to the present invention.

Referring now to FIG. 7, there is shown an exploded perspective view of the components of an attachment assembly 300 according to another preferred embodiment of the present invention. Telescoping attachment assembly 300 includes attachment base 330 and attachment tube 340. Dissection tool 350 is shown for the purpose of illustration. Attachment base 330 includes an attachment locking assembly 378 and a tool locking assembly 360 with a rotor shaft having gripping fingers 362. A spring 368 is disposed about the gripping fingers 362 along with a portion of locking sleeve 364. Locking sleeve 364 further includes an extension 366 and an external shoulder 370. As previously described above, attachment tube 340 includes several bearing assemblies adapted to rotationally support dissection tool 350. Proximal portion 343 includes a plurality of axially aligned grooves 344 adapted for mating with projections of the attachment base 330.

Figure 8B:
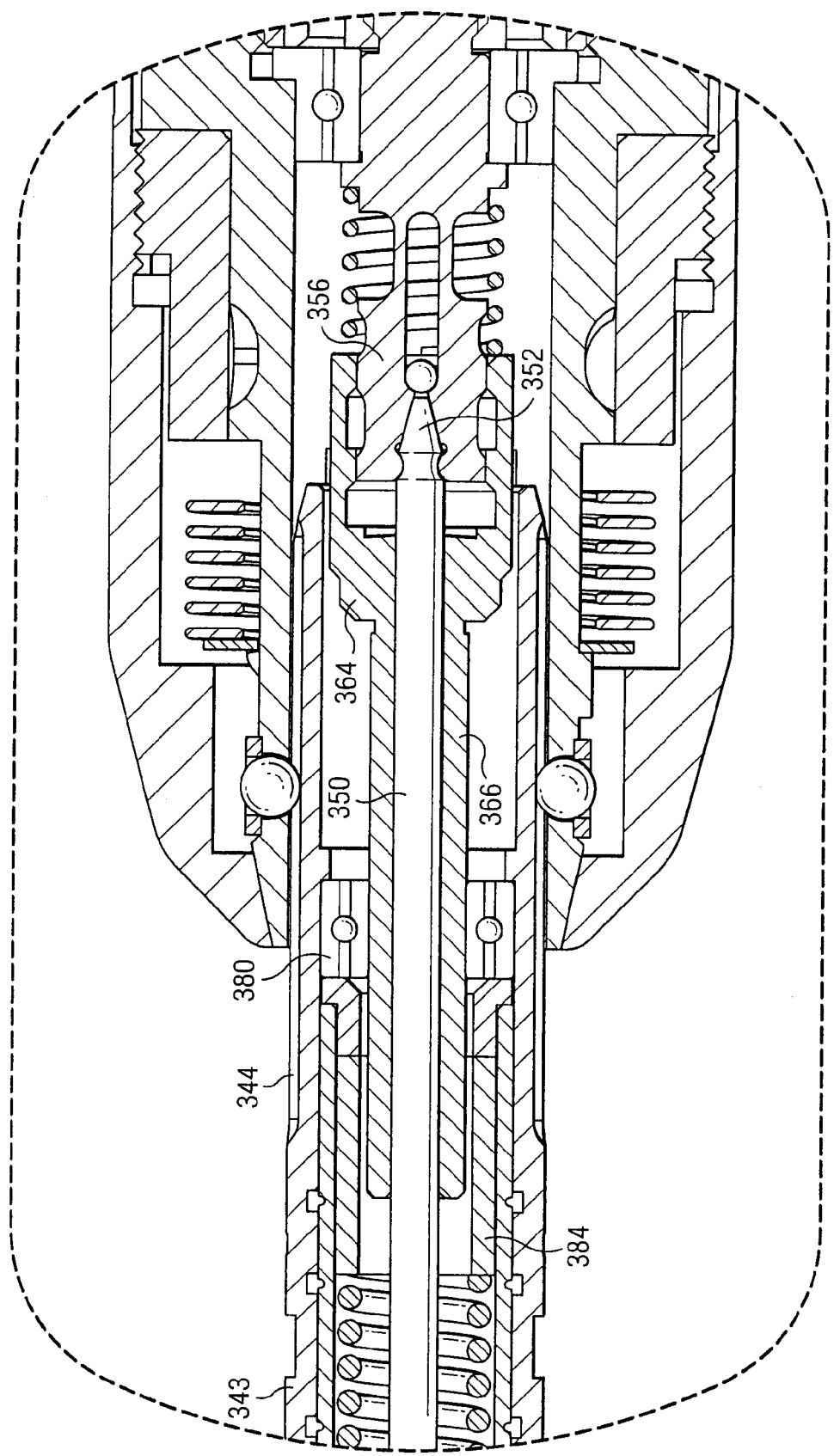

Referring now to FIGS. 8A and 8B, telescoping attachment 300 is shown with the tool locking assembly 360 and the attachment locking assembly 378 in the locked position suitable for active operation to use the dissection tool 350 to remove bone or other tissue. As shown in greater detail in FIG. 8B, locking sleeve 364 is moved distally such that internal projections of the sleeve are in substantial alignment with projection on the exterior of gripping fingers 362 to urge the collet to close on driving end 352 of dissection tool 350. The attachment tube proximal portion 343 is positioned within the attachment base 330 such that grooves 344 may be engaged by inwardly extending balls as previously described with respect to the embodiment of FIG. 3. The structure and operation of the attachment locking mechanism 378 is substantially identical to that described with respect to the embodiment of FIG. 3 and will not be further described herein.

Locking sleeve 364 includes a distally extending extension 366 having an internal bore with a diameter substantially matching the external diameter of tool 350 such that is provides support to the tool shaft during operation. It will be understood that locking sleeve 364 and extension 366 will turn with tool 350 during operation. Extension 366 extends within bearing 380 which is provided to isolate the rotation of extension 366 from attachment tube 340.

Figure 9B:
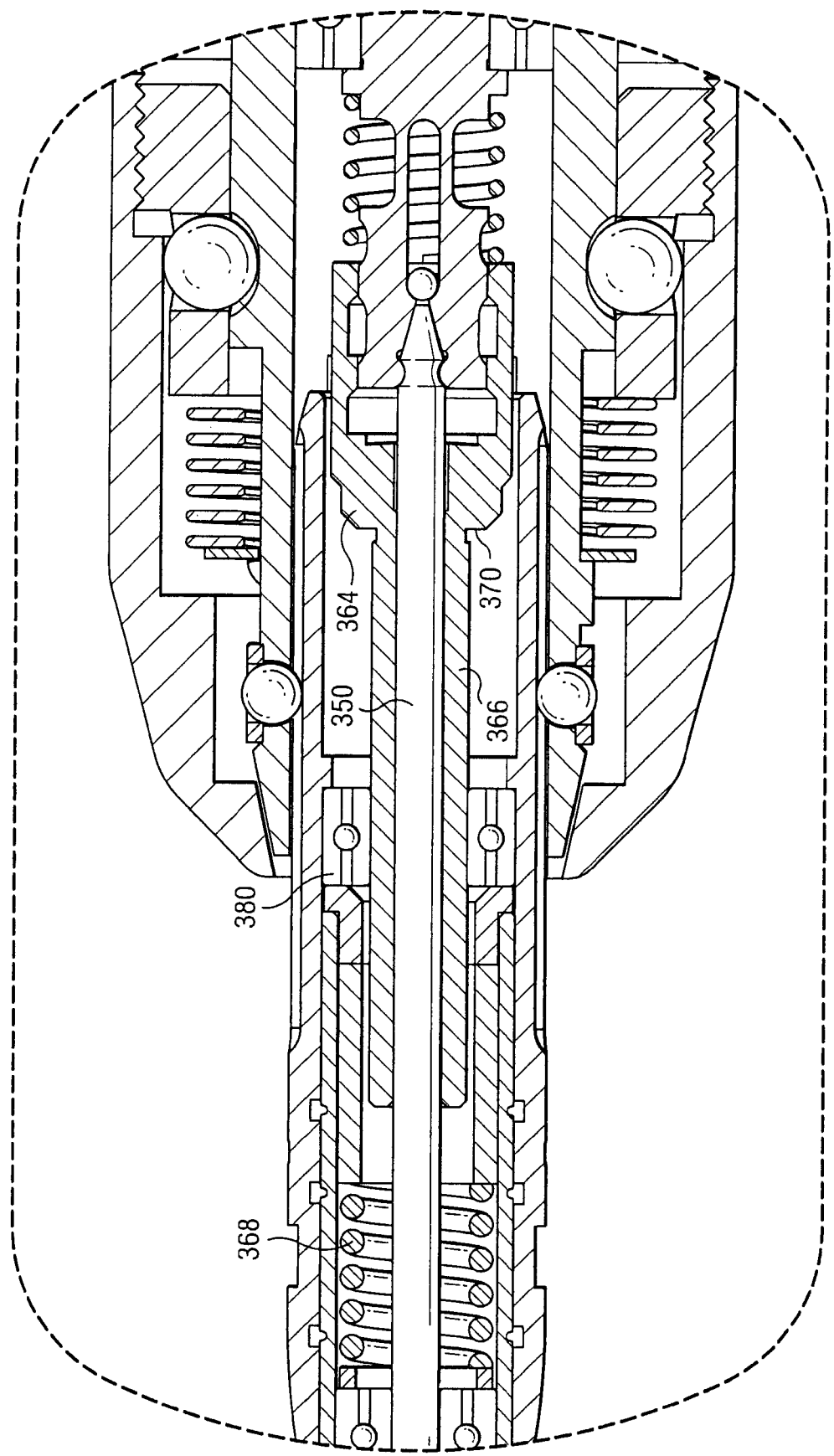

The telescoping attachment assembly 300 is shown in the attachment tube unlocked position and dissection tool locked position in FIGS. 9A and 9B. Locking sleeve 364 remains in the locked position to urge gripping fingers 362 to lockingly engage tool 350. Attachment tube 340 is free to move axially along the length of grooves 344. Bearing 380 is spaced from external shoulder 370 and extension 366 extends through bearing 380 and into sleeve 384. In this configuration, the distance between the distal end of attachment tube 340 and the attachment base 330 may be adjusted to the desired spacing.

Figure 10B:
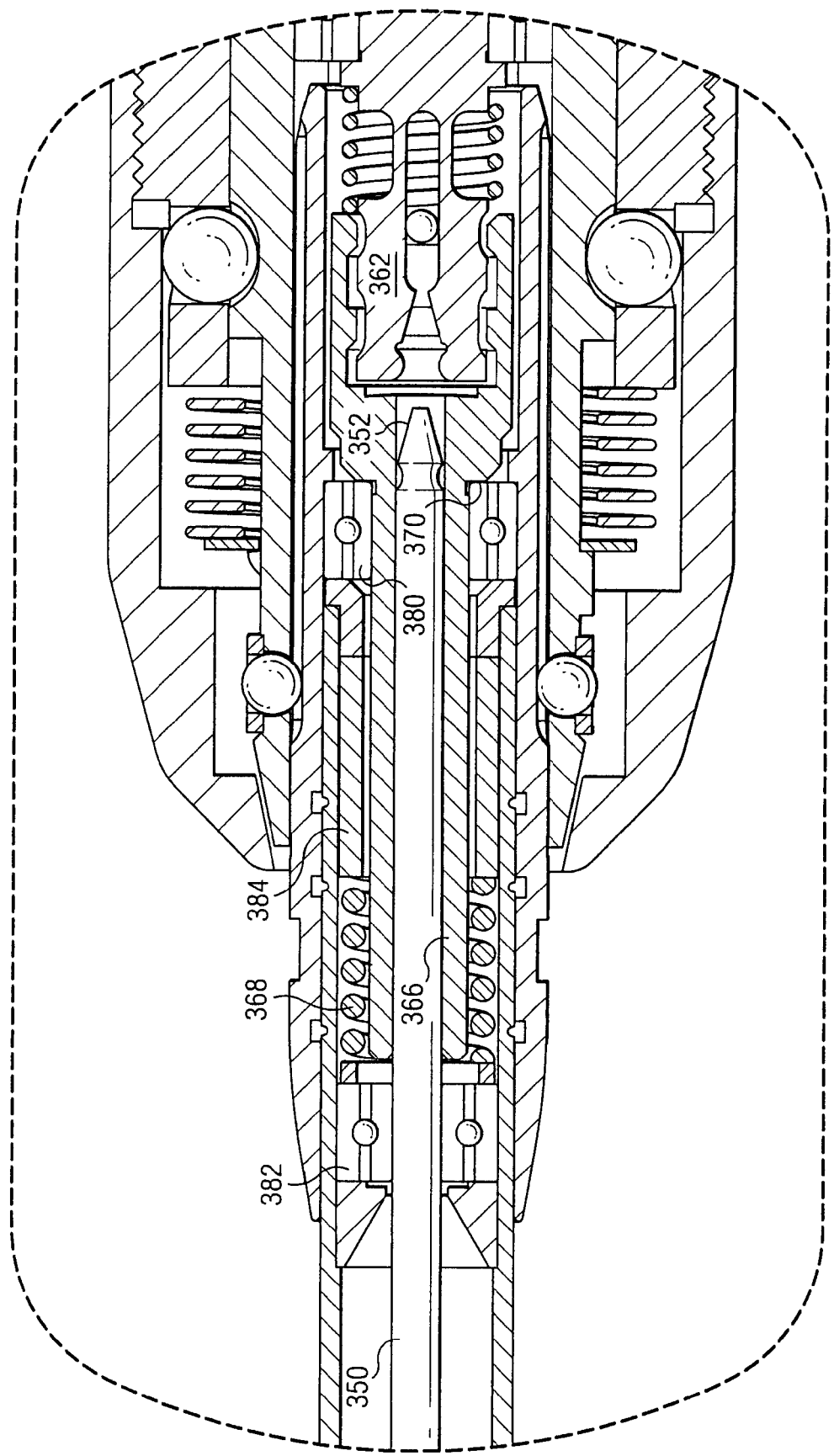

Referring now to FIGS. 10A and 10B, the telescoping attachment assembly 300 is shown with the attachment locking assembly 378 and the tool locking assembly 360 both in the unlock position. Attachment tube 340 has been moved proximally along the longitudinal axis toward attachment base 330 until bearing 380 abuts external shoulder 370 on locking sleeve 364. Further proximal movement of attachment tube 340 urges locking sleeve 364 to move to the unlock position shown in FIG. 10B thereby allowing gripping fingers 362 to move to an unlock position. Tool drive end 352 may then be removed from the tool collet. Extension 366 is sized to be received within bearing 380, sleeve 384 and spring 368. In the illustrated embodiment extension 366 does not contact bearing 382. It will be understood that distal movement of attachment tube 340 away from attachment base 330 will allow the spring biased locking sleeve 364 to move to the locked position.

The above description has been directed to a coupling assembly 30 that is detachable from motor 20, however; it is contemplated and hereby disclosed that coupler 30 may be integrated with motor 20 in a substantially integral unit. Still further, attachment tube 40 and dissection tool 50 have been shown as substantially straight components. It will be appreciated and is hereby disclosed that attachment tube 40 may be curved to accommodate various applications. It being understood that dissection tool 50 may have sufficient flexibility to conform to the curvature of the attachment along its length.

The above-described preferred embodiments of the present invention may be assembled and adjusted by manual manipulation of the outer surfaces of the components. It will be understood that in this preferred configuration, it is advantageous for the user such that additional instrumentation, tools or intricate movements are not required to accommodate the coupling and adjustment of the various components.

The above description of embodiments according to the invention is merely exemplary in nature and, thus, variations that do not depart from the gist of the invention are intended to be within the scope of the invention. Such variations are not to be regarded as a departure from the spirit and scope of the invention.

What is claimed is:

1. A surgical instrument, comprising:
a coupling assembly removably engaged with a motor assembly, the coupling assembly comprising an axial bore extending from a proximal portion of the coupling assembly to a distal portion of the coupling assembly along a longitudinal axis and comprising an attachment locking assembly adjacent the distal portion;
a tool-coupling assembly carried by the coupling assembly and positioned at least partially within the axial bore of the coupling assembly, the tool coupling assembly comprising an elastically deformable gripping member and a locking sleeve rotatably disposed about the gripping member and a rotor shaft engageable with the motor assembly and driveable when the coupling assembly is engaged with the motor assembly;
an attachment tube removably engaged with the attachment locking assembly of the coupling assembly and positioned at least partially within the axial bore of the coupling assembly, wherein in an unlocked state the attachment tube is movable with respect to the coupling assembly along the longitudinal axis and selectively engageable with the locking sleeve, and wherein in a locked state the attachment tube is displaced from the locking sleeve and is fixed with respect to the coupling assembly; and
a working tool comprising a shaft with a distal working portion and a proximal coupling portion, the working tool extending through the attachment tube and the axial bore of the coupling assembly such that the proximal portion of the working tool is removably engaged with the tool-coupling assembly,
wherein the rotor shaft of the tool-coupling assembly is structurally arranged to drive the working tool.

2. The surgical instrument of claim 1, wherein the coupling assembly includes a proximal housing portion and a distal housing portion, and wherein rotation of the proximal housing portion about the longitudinal axis selectively locks the coupling assembly to the motor assembly.

3. The surgical instrument of claim 2, wherein rotation of the proximal housing portion of approximately 90° about the longitudinal axis selectively locks the coupling assembly to the motor assembly.

4. The surgical instrument of claim 2, wherein rotation of the distal housing portion about the longitudinal axis selectively locks the attachment tube to the coupling assembly.

5. The surgical instrument of claim 4, wherein rotation of the distal housing portion of approximately 90° about the longitudinal axis selectively locks the attachment tube to the coupling assembly.

6. The surgical instrument of claim 1, wherein the attachment tube is movable along the longitudinal axis with respect to both the coupling assembly and the working tool when the proximal portion of the working tool is secured to the tool-coupling assembly.

7. The surgical instrument of claim 1, further comprising a first bearing assembly positioned within the attachment tube for supporting the shaft of the working tool.

8. The surgical instrument of claim 7, further comprising a second bearing assembly positioned within the attachment tube for supporting the shaft of the working tool, wherein the first bearing assembly is positioned adjacent a proximal portion of the attachment tube and the second bearing assembly is positioned adjacent a distal portion of the attachment tube.

9. The surgical instrument of claim 1, wherein at least a portion of the coupling assembly is movable along the longitudinal axis to selectively lock the coupling assembly to the motor assembly.

10. The surgical instrument of claim 1, wherein at least a portion of the coupling assembly is movable along the longitudinal axis to selectively lock the attachment tube to the coupling assembly.

11. The surgical instrument of claim 1, wherein the attachment tube is removably engaged with the attachment locking assembly of the coupling assembly via a projection-and-detent retention system.

12. The surgical instrument of claim 11, wherein an outer surface of the attachment tube comprises a plurality of elongated detents and wherein the attachment locking assembly includes at least one projection for mating with one or more of the plurality of elongated detents to form the projection-and-detent retention system.

13. The surgical instrument of claim 12, wherein in the unlocked state the at least one projection is slidable within the one or more of the plurality of elongated detents to permit movement of the attachment tube along the longitudinal axis with respect to the coupling assembly.

14. The surgical instrument of claim 12, wherein in the locked state the at least one projection is fixed within the one or more of the plurality of elongated detents to prevent movement of the attachment tube along the longitudinal axis with respect to the coupling assembly.

15. The surgical instrument of claim 1, wherein the motor assembly includes a tool chuck and the coupling assembly includes a work shaft, the work shaft removably engaged to the tool chuck.

16. The surgical instrument of claim 1, wherein rotation of the locking sleeve deforms the elastically deformable gripping member into engagement with the working tool.

17. The surgical instrument of claim 1, wherein translation of the attachment tube into the locking sleeve causes rotation of the locking sleeve moving the locking sleeve from a locked position to an unlocked position.

18. A surgical instrument having a motor assembly, comprising:
a coupling assembly removably engaged with the motor assembly, the coupling assembly comprising an axial bore extending from a proximal portion of the coupling assembly to a distal portion of the coupling assembly along a longitudinal axis, the coupling assembly comprising:
a tool-coupling assembly carried by the coupling assembly and positioned at least partially within the axial bore of the coupling assembly, the tool-coupling assembly comprising a pair of deformable gripping members having an engageable projection and a sleeve disposed about the deformable gripping members and rotatable relative thereto from a first unlocked position to a second locked position where the sleeve engages the engageable projection in the second locked position, a rotor shaft engageable with the motor assembly and driveable when the coupling assembly is engaged with the motor assembly, and
an attachment locking assembly adjacent the distal portion, the attachment locking assembly comprising one of a projecting engagement portion and a receiving portion disposed and sized to receive the projecting engagement portion;
an attachment tube removably engaged with the attachment locking assembly of the coupling assembly and positioned at least partially within the axial bore of the coupling assembly, the attachment tube comprising the other of the projecting engagement portion and the receiving portion, wherein in an unlocked state the attachment tube is movable with respect to the coupling assembly along the longitudinal axis, and engageable with the sleeve and wherein in a locked state the attachment tube is fixed with respect to the coupling assembly and displaced from the sleeve; and
a working tool comprising a shaft with a distal working portion and a proximal coupling portion, the working tool extending through the attachment tube and the axial bore of the coupling assembly such that the proximal portion of the working tool is removably engaged with the tool-coupling assembly,
wherein the rotor shaft of the tool-coupling assembly is structurally arranged to drive the working tool.

19. The surgical instrument of claim 18, wherein the projecting engagement portion and the receiving portion are respectively balls and axially extending grooves.

20. The surgical instrument of claim 18, wherein the rotor shaft comprises a gripping end sized and positioned to receive the proximal coupling portion of the working tool.

21. The surgical instrument of claim 18, wherein the coupling assembly includes a proximal housing portion and a distal housing portion, and wherein rotation of the proximal housing portion about the longitudinal axis selectively locks the coupling assembly to the motor assembly.

22. The surgical instrument of claim 21, wherein rotation of the distal housing portion about the longitudinal axis selectively locks the attachment tube to the coupling assembly.

23. The surgical instrument of claim 18, further comprising a spring coupled to the sleeve, said spring biasing the sleeve toward the second locked position.

* * * * *